(12) United States Patent
Pearlman (10) Patent No.: US 9,814,720 B2
(45) Date of Patent: Nov. 14, 2017

(54) COMPOSITIONS AND METHODS OF INHIBITING IL-17 EXPRESSION OF NEUTROPHILS

(71) Applicant: Case Western Reserve University, Cleveland, OH (US)

(72) Inventor: Eric Pearlman, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/837,893

(22) Filed: Aug. 27, 2015

(65) Prior Publication Data

US 2016/0058767 A1     Mar. 3, 2016

Related U.S. Application Data

(60) Provisional application No. 62/042,516, filed on Aug. 27, 2014.

(51) Int. Cl.
*A61K 31/519* (2006.01)
*A61K 45/06* (2006.01)
*A61K 31/381* (2006.01)
*A61K 31/426* (2006.01)

(52) U.S. Cl.
CPC .......... *A61K 31/519* (2013.01); *A61K 31/381* (2013.01); *A61K 31/426* (2013.01); *A61K 45/06* (2013.01)

(58) Field of Classification Search
CPC .................................................. A61K 31/519
USPC .................................................... 514/265.1
See application file for complete search history.

(56) References Cited

U.S. PATENT DOCUMENTS 4,613,587 A * 9/1986 Kessler ................ A61K 9/0048
514/15.5
8,058,316 B2   11/2011 Farjo 2013/0267463 A1   10/2013 Youn et al.
2013/0287815 A1 * 10/2013 Manel ................ C12N 5/0636
424/278.1
2014/0163001 A1    6/2014 Yamamoto et al.
2014/0187554 A1    7/2014 Kamenecka et al.

OTHER PUBLICATIONS

Karthikeyan et al. Journal of Infectious Diseases (2011), 204(6), 942-950.*
Zaidi et al. Infection and Immunity (2012), 80(10), 3706-3712.*
Abraham et al. Cancer Biology & Therapy, 2011, 12(12), 1019-1022.*
Ktoltz et al. Clinical Microbiology Reviews, 0893-8512/00/$04.0010 Oct. 2000, p. 662-685.*
Leal, Case Western Reserve University (0042), Dissertation Abstracts International, (2012) vol. 74, No. 3B(E).*
Zhou et al. Nature Immunology, 2007, 8(9), 967-974.*
Mu et al. Cellular Microbiology, 2011, 13(3), 374-387.*
Patricia R Taylor, et al., "Autocrine IL-17A-IL-17RC neutrophil activation in fungal infections is regulated by IL-6, IL-23, RORγT and Dectin-2", Manuscript, Feb. 2014, pp. 143-151.
Patricia R. Taylor, et al., "STAT3 phosphorylation mediates RORγt translocation and IL-17 expression in neutrophils, eliciting enhanced fungal killing", Department of Opthalmology and Visual Sciences and Department of Rheumatology, Case Western Reserve University, Cleveland, OH.
Laura A. Solt, et al., "Suppresion of TH17 differentiation and autoimmunity by a synthetic ROR ligand", Apr. 28, 2011, vol. 472, pp. 491-494.

* cited by examiner

*Primary Examiner* — Nizal Chandrakumar
(74) *Attorney, Agent, or Firm* — Tarolli, Sundheim, Covell & Tummino LLP

(57) ABSTRACT

A method of inhibiting IL-17 expression in neutrophils of a subject in need thereof includes administering to neutrophils of the subject a therapeutically effective amount of agent that inhibits STAT3 mediated IL-17 expression in the neutrophils of the subject.

4 Claims, 6 Drawing Sheets

COMPOSITIONS AND METHODS OF INHIBITING IL-17 EXPRESSION OF NEUTROPHILS

RELATED APPLICATION

This application claims priority from U.S. Provisional Application No. 62/042,516, filed Aug. 27, 2014, the subject matter of which is incorporated herein by reference in its entirety.

TECHNICAL FIELD

This application relates to compositions and methods for inhibiting IL-17 expression in neutrophils and particularly relates to compositions and methods for use in the treatment of corneal ulcers from fungal keratitis.

BACKGROUND

Following an insult to the cornea, the immune and inflammatory systems respond to protect the integrity of the eye. This protective mechanism can have clinical manifestations ranging from cellular infiltration to ulcer formation. Though protective, these processes often compromise the primary function of the eye by causing vascularization, scarring and/or perforation of the cornea.

When there is an insult to the corneal surface, inflammatory and/or immune cells are sent to repair the damage. These cells can aggregate in a region of the cornea and are visible as clinically identifiable infiltrates. This infiltrate formation and resultant corneal inflammation can arise from either infectious or non-infectious conditions. One infectious condition that can adversely affect the cornea is fungal keratitis. Major causes of fungal keratitis in the USA and worldwide include infection by *Fusarium* and *Aspergillus* species. In developing countries, fungal keratitis is primarily associated with trauma related to agricultural work; whereas, in industrialized countries, fungal keratitis is associated with contact lens wear.

Currently, steroid use is the only treatment for corneal infiltrates. The side effects of steroid use are considerable. In infectious keratitis, steroids are given only after resolution of infection; otherwise, they can have an adverse effect on the infection. Furthermore, steroid use can cause increased ocular pressure, thereby increasing the risk of glaucoma, and are often administered together with anti-glaucoma treatment.

SUMMARY

Embodiments described herein relate to compositions and methods for use in inhibiting IL-17 expression in neutrophils, and particularly relate to compositions and methods for use in inhibiting IL-17 expression of neutrophils of peripheral blood of a cornea of a subject. The inhibition of IL-17 expression of the neutrophils can be used to treat corneal ulcers resulting from fungal keratitis in the subject.

In some embodiments, the methods include administering to peripheral blood of the subject a therapeutically effective amount of an agent that inhibits STAT3 mediated IL-17 expression in neutrophils of the peripheral blood of the subject. In some embodiments, the agent can include a STAT3 inhibitor that inhibits STAT3 phosphorylation of STAT3 of neutrophils of the subject. In other embodiments, the agent can include a RORγt inhibitor that inhibits STAT3 mediated RORγt translocation to the nucleus of neutrophils of the subject.

BRIEF DESCRIPTION OF THE DRAWINGS

FIGS. 1(A-E) illustrate IL-17A expressing peripheral blood neutrophils. Intracellular IL-17A (A, B) and Il17a gene expression (C, D) in peripheral blood neutrophils from fungal keratitis patients, cohorts and regional controls. A. Representative flow cytometry profiles showing peripheral blood neutrophils from a fungal keratitis patient after intracellular staining for IL-17. Neutrophils showing intracellular IL-17 by fluorescence microscopy (multi-lobed nuclei are visible after DAPI staining, and a representative H&E stain shows a highly purified population of neutrophils). B. Percent IL-17+ neutrophils in peripheral blood of *Aspergillus* and *Fusarium* keratitis patients (combined), and from cohorts and regional controls (mean+/−SEM). Data points represent individuals. C. IL-17 negative neutrophils in the same field as IL-17 positive cells (arrowhead). D. Il17a transcripts in peripheral blood neutrophils normalized to β-actin calculated by $2^{-\Delta\Delta ct}$ as described in the methods. Data are shown as mean+/−SEM of the ratio of each patient to the mean of cohorts (patients vs. cohorts) or to the mean of regional controls (patients vs. controls). Data also show the ratio of each cohort to the mean of regional controls (cohorts vs. controls). E. Representative neutrophils from a corneal ulcer showing intracellular IL-17. Original magnification of fluorescent images is ×600; for H&E is ×200.

FIGS. 2(A-C) illustrate plots showing plasma levels of IL-6, IL-23 and IL-17. A. Plasma was collected from fungal keratitis patients (n=93), cohorts (n=15), and regional controls (n=20), and cytokines were measured by ELISA. Data points represent individuals (mean+/−SEM). B. Spearman's rank correlation coefficient of 45 individuals (combined patients, cohorts and regional controls) comparing percent IL-17+ peripheral blood neutrophils with plasma IL-17, IL-23 or IL-6 from each individual. C. Correlation between plasma IL-17 and plasma IL-6 and IL-23 (n=121).

FIGS. 3(A-G) illustrate phosphorylation of STAT3 in vivo- (A) Representative histograms displaying purity of murine NIMP-R14+ bone marrow neutrophils recovered 3 days after subcutaneous injection of heatkilled, swollen *Aspergillus fumigatus* conidia (primed) or of naïve C57BL/6 mice. (B) Percent positive intracellular STAT3 or p-STAT3 in NIMP-R14+ bone marrow cells from naïve or primed C57BL/6. The black color represents the isotype control; the red represents naïve; and blue, primed neutrophils. (C) Western blot of total cell lysates from isolated bone marrow neutrophils from naïve (N) or primed C57BL/6 mice. Membranes were probed with antibodies reactive with STAT3 (Total STAT3), p-STAT3 (Tyr 705), and β-actin. (D) Il17a gene expression in naïve (N) or primed C57BL/6 bone marrow neutrophils. Actb (which encodes β-actin) served as the control for gel loading. (E) Naïve or primed C57BL/6 mice were infected with RFP *Aspergillus*, Cornea cells of 10 corneas were pooled and total NIMP-R14+-positive neutrophils in the cornea were gated for further STAT3 analysis. Percent of neutrophils in cornea suspensions is displayed above histogram peak. Flow cytometry analysis of Total STAT3/p-STAT3 (Tyr 705) (F), and p-STAT3/IL-17A (G) of neutrophil gated cornea cells. (ab): Representative histograms from (5 mice/group); Each experiment was repeated twice with similar results.

FIGS. 4(A-G) illustrate phospho-STAT3-dependent RORγt nuclear translocation and IL-17 expression by murine neutrophils- (A) Western blot of total cell lysates of isolated bone marrow neutrophils from naïve C57BL/6 mice after 1 h stimulation with recombinant murine (rm)IL-6 (20 µg/ml) and/or rIL-23 (2 µg/ml). Membranes were probed with antibody to STAT3, p-STAT3, and β-actin. (B) Intracellular p-STAT3 and IL-17A expression in naïve or IL-6/23-stimulated neutrophils. (C) Scatter plots of total STAT3+/pSTAT3+ bone marrow neutrophils unstimulated, or stimulated with recombinant mouse IL-6 and IL-23 with or without p-STAT3 inhibitor Stattic or INC424. (D) Representative confocal images of intracellular RORγt in IL-6/23-stimulated +/−phospho-STAT3 inhibitor Stattic or INC424 in C57BL/6 neutrophils and counterstained with DAPI. Original magnification, ×1000. Il17a gene expression (E), quantification of IL-17A protein by ELISA (F), and intracellular IL-17A production (G) in unstimulated (Unstim), IL-6/23 stimulated, or IL-6/23-stimulated plus p-STAT3 inhibited (IL-6/23+Stattic, IL-6/23+INC424), or IL-6/23-stimulated plus RORγt inhibitor (IL-6/23+SR1001) bone marrow neutrophils of C57BL/6 mice. (E) Actb was used as a loading control. Three experiments were performed with similar results.

FIGS. 5(A-D) illustrate the role of p-STAT3 in human peripheral blood neutrophils- (A) Western blot of total cell lysate of purified human neutrophils stimulated with recombinant human IL-6 and rhIL-23 with/without p-STAT3 inhibitor, Stattic or INC424. Blots were probed with antibodies to p-STAT3, total STAT3, RORγt, and β-actin. (B) Nuclear extracts of human neutrophils incubated with rhIL-6+rhIL-23 and p-STAT3 inhibitors. Blots were probed with anti-RORγt or with a loading control (TBP). (C) Confocal images of RORγt and DAPI in human neutrophils from a single donor. Original magnification, ×1000. (D) Total cellular IL-17A protein of human neutrophils stimulated with recombinant human IL-6 and IL-23 and incubated with p-STAT3 inhibitors, Stattic or INC424, or RORγt inhibitor SR1001. (E) Il17a gene expression by neutrophils incubated 1 h with recombinant human IL-6 and rhIL-23 (IL-6/23) plus p-STAT3 inhibitors Stattic or INC424 (IL-6/23+Stattic, IL-6/23+INC424), or RORγt activity, SR1001 (IL-6/23+SR1001). Neutrophils were stimulated with recombinant human IL-6 (20 µg/ml) and rhIL-23 (2 µg/ml). Experiments were repeated 2 times with neutrophils from same donor.

FIGS. 6(A-F) illustrate the role of p-STAT3, RORγt, IL-17RC, and IL-17A in the production of neutrophil reactive oxygen species (ROS) and hyphal growth in vitro-(A,B) IL-17RC gene expression in purified murine (A) or human (B) neutrophils unstimulated (US) or stimulated with recombinant IL-6 and IL-23 (IL-6/23), plus p-STAT3 inhibitors (IL-6/23+Stattic or IL-6/23+INC424), or RORγt inhibitor (IL-6/23+SR1001). (C: upper panel) ROS production (intracellular CFDA) in bone marrow neutrophils from naïve C57BL/6 mice, or stimulated 3 h with IL-6+IL-23, plus Stattic, INC424, or SR1001 then incubated for 1 h with growing *Aspergillus* hyphae+/−rIL-17A. RFU: Relative fluorescent units; MFI: Mean fluorescent intensity. (D: lower panel) Fungal growth of dsRed expressing *Aspergillus* after 18 h incubation with each neutrophil population. Fungal mass was measured by fluorimetry of dsRed, and represented as RFU. Mean+/−SD of 3 samples per group; controls are medium only (no neut) and unstimulated neutrophils (unstim). (E: upper panel) ROS production, and (f: lower panel) fungal mass of human peripheral blood neutrophils incubated with *Aspergillus* hyphae+/−rhIL-17A, or p-STAT3 inhibitors, Stattic or INC424, or RORγt inhibitor SR1001. (A) Actb (encodes β-actin) was used as the loading control. (B) GAPDH was used as the loading control. (C-D, E-F) mean+/−SD of 3 wells per experimental condition from neutrophils pooled from 3 mice per group (C-D) or from a single donor (E-F). Data are representative of two separate experiments.

FIGS. 7(A-E) illustrate Phospho-STAT3 as a regulator of RFP-*Aspergillus* hyphal growth in vivo-INC424 was administered by oral gavage twice a day for 5 days to block phosphorylation of STAT3 in naïve C57BL/6 mice. Mice were then primed with heat-killed, swollen *A. fumigatus* 3 days prior to inducing corneal infection. (A) Total bone marrow cells were analyzed by flow cytometry to confirm systemic phospho-STAT3 inhibition, 24 h post-infection. (B) Primed (CTRL) and p-STAT3 inhibited-and primed (α-STAT3) mice infected with RFP *Aspergillus* showing representative corneas 24 h post-infection, and total RFP in infected corneas assessed by image analysis (data points represent individual corneas). Original magnification, ×20. Total NIMPR14+ neutrophils (C); IL17a gene expression (D); intracellular IL-17A/p-STAT3 positive cornea cells (E). Experiments were performed in two separate experiments with similar results.

DETAILED DESCRIPTION

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the term "subject" refers to any warm-blooded organism including, but not limited to, human beings, pigs, rats, mice, dogs, goats, sheep, horses, monkeys, apes, rabbits, cattle, etc.

As used herein, the terms "treatment," "treating," or "treat" refers to any specific method or procedure used for the cure of, inhibition of, reduction of, elimination of, or the amelioration of a disease or pathological condition (e.g. corneal ulcer) including, for example, preventing corneal ulcers from fungal infection from developing, inhibiting corneal ulcers from fungal infection development, arresting development of clinical symptoms associated with fungal infection, and/or relieving the symptoms associated with fungal infection.

As used herein, the term "effective amount" refers to a dosage of an agent described herein protein inhibitor administered alone or in conjunction with any additional therapeutic agents that are effective and/or sufficient to provide treatment of the corneal ulcer, fungal infection and/or a disease or disorder associated with fungal infection. The effective amount can vary depending on the subject, the disease being treated, and the treatment being effected.

As used herein, the term "therapeutically effective amount" refers to that amount of agent described herein used alone and/or in combination with additional therapeutic agents that results in amelioration of symptoms associated with the corneal ulcer, fungal infection and/or a disease or disorder associated with fungal infection and/or results in therapeutically relevant effect. By way of example, a "therapeutically effective amount" may be understood as an amount of an agent described herein required to treat a corneal ulcer from a fungal infection in a subject.

As used herein, the terms "parenteral administration" and "administered parenterally" refers to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

As used herein, the terms "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

As used herein, "unit dosage" formulations are those containing a dose or sub-dose of the administered ingredient adapted for a particular timed delivery. For example, "unit dosage" formulations are those containing a daily dose or unit or daily sub-dose or a weekly dose or unit or weekly sub-dose and the like.

Embodiments described herein relate to compositions and methods for use in inhibiting IL-17 expression in neutrophils, and particularly relate to compositions and methods for use in inhibiting IL-17 expression of neutrophils of peripheral blood of a cornea of a subject. The inhibition of IL-17 expression of the neutrophils can be used to treat corneal ulcers resulting, for example, from fungal keratitis in the subject.

In some embodiments, a method of treating corneal ulcers associated with or from fungal keratitis can include administering to peripheral blood of the subject a therapeutically effective amount of an agent that inhibits STAT3 mediated IL-17 expression in neutrophils of the peripheral blood of the subject.

The agent that inhibits STAT3 mediated IL-17 expression in neutrophils of the peripheral blood of the subject can include any agent, such as a small molecule, polypeptide, polynucleotide, that is capable of substantially reducing, inhibiting, blocking, and/or mitigating STAT3 mediated IL-17 expression in neutrophils and particularly fungal induced STAT3 mediated IL-17 expression in neutrophils.

In some embodiments, the agent can include a STAT3 inhibitor that inhibits STAT3 phosphorylation of STAT3 of neutrophils of the subject. Examples of STAT3 inhibitors include Stattic and Ruxolitnib (INC424). Still other examples of STAT3 inhibitors include tyrphostins, in particular AG-490, and inhibitors of Jak, Src, and BCR-Abl tyrosine kinases. Other tyrphostins suitable for use herein include, but are not limited to, AG17, AG213 (RGS0864), AG18, AG82, AG494, AG825, AG879, AG1112, AG1296, AG1478, AG126, RG13022, RG14620, AG555, and related compounds. Other examples of STAT3 inhibitors are disclosed in U.S. Pat. Nos. 8,816,056, 8,796,320, 8,791,067, 8,779,151, 8,779,001, 8,466,290, 8,263,599, 8,058,316, 7,888,395, and 7,342,095, all of which are incorporated herein by reference in their entirety.

In other embodiments, the agent can include a retinoid-related orphan receptor (ROR)γt inhibitor that inhibits STAT3 mediated RORγt translocation to the nucleus of neutrophils of the subject. Examples of RORγt inhibitors include SR1001, TO901317, Digoxin, SR1078, Ursolic acid, 7-hydroxycholesterol, 24-ketocholesterol, 24S-hydroxycholesterol, as well as other RORγt inhibitors described in U.S. Patent Application Publication Nos. 2014/0228409 and 2014/0163001, which are herein incorporated by reference in their entirety.

In some embodiments, the methods may be used to treat corneal ulcers from fungal keratitis. Fungal keratitis may be related to fungal genera including, for example, *Fusarium, Penicillium, Aspergillus, Cephalosporium (Acremonium), Curvularia, Altemaria, Trichophyton, Microsporum, Epidermophyton, Scopulariopsis*, and *Candida*.

The agents used in the methods described herein can be administered to the peripheral blood of the subject using standard methods including, for example, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Treatment according to the present methods of the invention can be altered, stopped, or re-initiated in a subject depending on the status of fungal infection (e.g., corneal fungal infection). Treatment can be carried out as intervals determined to be appropriate by those skilled in the art. For example, the administration can be carried out 1, 2, 3, or 4 times a day.

The methods can include administering to the subject a therapeutically effective amount of the agent. Determination of a therapeutically effective amount is within the capability of those skilled in the art. The exact formulation, route of administration, and dosage can be chosen by the individual physician in view of the subject's condition.

Formulation of pharmaceutical compounds for use in the modes of administration noted above (and others) are described, for example, in *Remington's Pharmaceutical Sciences* (18$^{th}$ edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In an exemplary embodiment, the agent can be provided in a parenteral preparation, e.g., injection or intravenous preparation, that can be administered to the peripheral blood of the subject to inhibit IL-17 expression in neutrophils.

In other embodiments, the agent can be provided in an ophthalmic preparation that includes a pharmaceutically acceptable solution, suspension, or ointment. Some variations in concentration can occur, depending on the particular agent employed, the condition of the subject to be treated and the like, and the person responsible for treatment can determine the most suitable concentration for the individual subject.

Subjects affected with corneal fungal infection (or at risk of corneal fungal infection) which are not readily accessible or suitable for ophthalmic (e.g. eye-drops) and/or topical administration, can be treated by a systemic approach, such as intravenous infusion. For example, the agent can be administered at a low dosage by continuous intravenous infusion. In another example, in which a patient requires longer-term care, the agent can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

In yet another aspect, the agents that inhibit STAT3 mediated IL-17 expression in neutrophils can be administered as part of a combinatorial therapy with additional therapeutic agents. The phrase "combinatorial therapy" or "combination therapy" embraces the administration of an agent that inhibits STAT3 mediated IL-17 expression in neutrophils, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

For example, the combinational therapy can include the administration of an agent that inhibits STAT3 mediated IL-17 expression in neutrophils with at least one antibacterial, antiviral or antifungal agent to treat a microbial infection and related inflammation (e.g., corneal inflammation) in a subject. Antibiotic agents administered in conjunction with an agent that inhibits STAT3 mediated IL-17 expression in neutrophils or pharmaceutical composition can include, but are not limited to aminosalicylic acid, nalidixic acid, amoxicillin, amoxicillin and potassium clavulanate, ampicillin, ampicillin and sulbactam, azithromycin, bacampicillin, carbenicillin indanyl sodium (and other carbenicillin salts), capreomycin, cefadroxil, cefazolin, cephalexin, cephalothin, cephapirin, cephaclor, cefprozil, cephadrine, cefamandole, cefonicid, ceforanide, cefuroxime, cefixime, cefoperazone, cefotaxime, cefpodoxime, ceftazidime, ceftibuten, ceftizoxime, ceftriaxone, cefepime, cefmetazole, cefotetan, cefoxitin, ciprofloxacin, clarithromycin, clindamycin, clofazimine, cloxacillin, co-trimoxazole, cycloserine, dicloxacillin, dirithromycin, erythromycin (and erythromycin salts such as estolate, ethylsuccinate, gluceptate, lactobionate, stearate), ethambutol-HCl and other salts, ethionamide, fosfomycin, gentamycin (fortified with vancomycin for methicillin-resistant *Staphylococcus aureus* (MRSA) infections) imi-penem, isoniazid, levofloxacin, lomefloxacin, loracarbef, methicillin, methenamine, metronidazole, mezlocillin, nafcillin, nitrofurantoin, norfloxacin, novobiocin, ofloxacin, oxacillin, penicillin V, penicillin salts, penicillin complexes, pentamidine, piperacillin, piperacillin and tazobactam, sparfloxacin, sulfacytine, sulfamerazine, sulfamethazine, sulfamethizole, sulfasalazine, sulfisoxazole, sulfapyrazine, sulfadiazine, sulfinethoxazole, sulfapyridine, ticarcillin, ticarcillin and potassium clavulanate, trimethoprim, trimetrexate, troleandomycin, $4^{th}$ generation fluroquinoline like moxifloxacin or gatifloxacin, cefazolin or vancomycin and fluoroquinolone vancomycin and mixtures thereof.

In one specific example, the combinational therapy includes an agent that inhibits STAT3 mediated IL-17 expression in neutrophils and at least one ophthalmic antibiotic or ophthalmic antiviral. Ophthalmic antibiotics include, for example, chloramphenicol sodium succinate ophthalmic (chloramphenical); CORTISPORIN (neomycin and polymyxin β sulfates and hydrocortisone acetate cream); ILOTYCIN (erythromycin ophthalmic ointment); NEODECADRON (neomycin sulfate-dexamethasone sodium phosphate); POLYTRIM (trimethoprim and polythyxin β sulfate opthalmic solution); TERRA-CORTRIL (oxytetracycline HCL and hydrocortisone acetate); TERRAMYCIN (oxytetratcycline); and TOBRADEX (tobramycin and dexamethosone ophthalmic suspension and ointment).

Ophthalmic antivirals include, for example, VIRA-A ophthalmic ointment, (vidarabine). Opthalmic quinalones include, for example, CHIBROXIN (norfloxacin ophthalmic solution); CILOXAN ophthalmic solution, (Ciprofloxacin HCL); and Ocuflox ophthalmic solution (ofloxacin). Opthalmic sulfonamides include, for example, BLEPHAMIDE ophthalmic ointment (sulfacetamide sodium and prednisolone acetate); and BLEPHAMIDE ophthalmic suspension (sulfacetamide sodium and prednisolone acetate).

Additionally, an agent that inhibits STAT3 mediated IL-17 expression in neutrophils may be administered to a subject for the treatment of a corneal ulcer from a fungal infection in combination with one or more other antifungal agents, such as a polyenic derivative (e.g. Amphotericin B, Nystatin, a lipid formulation of Amphotericin B, filipin and/or pimaricin (Natamycin)), 5-fluctyosine, an azole derivative (e.g., Voriconazole Fluconazole, Intraconazole, Ketoconazole, Miconazole, Clotrimazole, ZD-08070, UK-109496, SCH 56592), 5 Fluorocytosine, a Pneumocandin or Echinocandin derivative such as Cilofungin, LY-303366, L 733560, or L-743872. In an exemplary embodiment, an ophthalmic preparation administered to a subject for the treatment of a corneal fungal infection and related inflammation includes STAT3 inhibitor with natamycin (5% (w/w)), voriconazole (1% w/w) and/or amphotericin B (0.3% (w/w)).

The invention is further illustrated by the following example, which is not intended to limit the scope of the claims.

Example 1

The following example shows IL-17 producing neutrophils are generated in individuals exposed to high levels of airborne spores. The level of IL-17 expressing neutrophils were determined in fungal keratitis patients and healthy cohorts in an agricultural region of south India.

Methods

Peripheral Blood Neutrophils

Peripheral blood was suspended in 3% Dextran, and plasma was separated by centrifugation. Neutrophils were isolated using Lymphoprep, and suspended in complete RPMI (all reagents from Sigma St. Louis, Mo.). Giemsa staining showed >95% neutrophils.

Flow Cytometry

Neutrophils were incubated with Fc blocking reagent (eBioscience) at 4° C. for 30 minutes. For intracellular staining, cells were fixed with 4% PFA, incubated with 1× permeabilization buffer (eBioscience), and incubated 1 h with rabbit serum (Vector laboratories) to block Fc receptors. Neutrophils were then incubated with anti-IL-17 or isotype control (eBiosciences), and analyzed on a BD FACS Calibur platform using CellQuest software, using FlowJo (Tree Star) software. Gates and quadrants were determined by the isotype controls.

Immunofluorescence

For direct immunofluorescent staining, intracellular IL-17 was detected in neutrophils after incubating with antibodies as described above. Peripheral blood neutrophils were centrifuged on to charged microscope slides using a Cytospin, and Vectashield media with DAPI was added (Vector Labs). Infected corneal ulcer material was spread onto a microscope slides as we described previously. IL-17 positive and negative cells were detected by fluorescence microscopy.

Quantitative PCR

Q-PCR for IL-17 was performed, normalized for β-actin expression, and $2^{-\Delta\Delta ct}$ was calculated.

Plasma Cytokines

Cytokines in plasma were analyzed by ELISA according to the manufacturer's protocol (R&D).

Statistical Analysis

Statistical analyses were performed using a one-way ANOVA and Bonferroni's Multiple Comparison Test or a Spearman's rank correlation coefficient analysis (Prism, GraphPad Software V5.0 (San Diego, Calif.)). A p-value <0.05 was considered significant.

Results

Study Populations

A total of 128 subjects were enrolled and assigned to one of three groups: fungal keratitis patients, cohorts with high exposure to airborne conidia but no disease, and healthy controls who live and work in a facility with filtered air. Of the 93 patients with corneal ulcers, 59 were caused by *Fusarium* and 34 were caused by *A. flavus*. The mean age of each group was 45.75±13.10 (patients), 36.73±12.56 years (cohorts) and 31.78±9.45 (controls). Fungal keratitis patients had no other disease symptoms.

Intracellular IL-17 in Peripheral Blood and Corneal Neutrophils

A recent study showed that peripheral blood neutrophils from healthy individuals in the USA do not express or produce IL-17. To determine IL-17 expression in peripheral blood neutrophils from fungal keratitis patients or from healthy individuals exposed to high levels of airborne spores, highly purified populations of neutrophils were examined.

Figure 1A:
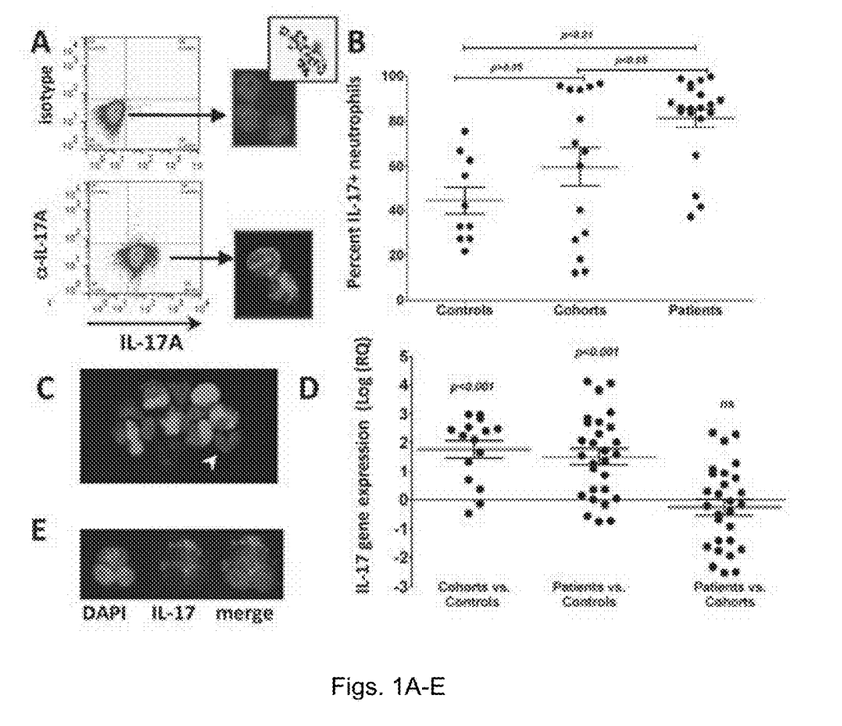

As shown in FIG. 1A, a distinct population of IL-17 producing neutrophils was identified by flow cytometry, and confirmed by fluorescence microscopy. Consistent with our prior findings comparing *Fusarium* and *Aspergillus* responses, there was no significant difference in the percentage of IL-17-producing neutrophils between *Fusarium* and *Aspergillus* infected patients (data not shown); therefore we pooled these patients for comparison with cohort and control groups. The percentage of IL-17-producing neutrophils in fungal keratitis patients was significantly higher than cohorts and controls (mean+/−SD is 80.9±19.2% for patients vs. 59.6±31.9% for cohorts, and 48.1±19.7 for controls, p<0.05 between patients vs. cohorts or controls, FIG. 1B). In contrast, there was no significant difference in the percent of IL-17-producing neutrophils between cohorts and regional controls. IL-17 negative neutrophils were detected in the same field as positive cells (FIG. 1C), indicating that the intracellular IL-17 reactivity was specific.

To examine IL-17 gene expression, RNA was extracted from peripheral blood neutrophils, and Il17a expression was assessed by quantitative PCR. Il17a was detected in individuals from each group; however, the $^{\Delta\Delta}$ct scores were significantly higher in patients and cohorts compared with regional controls, whereas there were no significant differences between cohorts and patients (FIG. 1D). IL-17 was also detected in neutrophils from corneal ulcers of fungal keratitis patients (FIG. 1E).

Overall, these data show that peripheral blood neutrophils from individuals in each group express IL-17 transcripts and protein, although expression was statistically higher in the patient group.

Plasma IL-6, IL-23 and IL-17

Figure 2A:
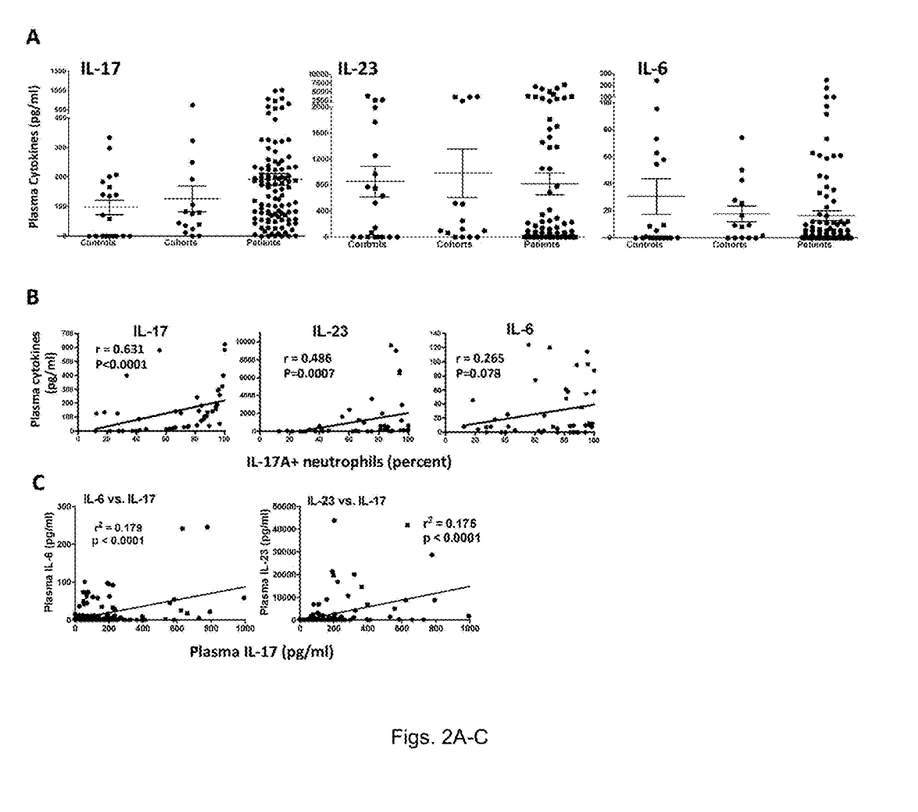

As IL-6 and IL-23 induce IL-17 gene expression in human and murine neutrophils, we examined IL-6, IL-23 and IL-17 levels in the plasma of fungal keratitis patients compared with cohorts and regional controls. FIG. 2A shows that the concentration of IL-17 in patients was 190.8±200.3 pg/ml, 125.6±167.1 pg/ml in cohorts, and 96.4±108.3 pg/ml in regional controls. Although the mean value of IL-17 was higher in patient samples, there were no significant differences among any of the groups. Similarly, there were no significant differences among the groups in plasma IL-23 and IL-6 (FIG. 2A).

To determine if there is a correlation between plasma levels of IL-17, IL-23 or IL-6 and IL-17 producing neutrophils, we performed Spearman correlation coefficient analyses on all 45 individuals where we had percentage neutrophil data (combining patients, cohorts and controls) with their corresponding plasma cytokine concentrations. We found a correlation between the IL-17 producing neutrophils and the concentration of plasma IL-17 (p<0.0001), and plasma IL-23 (p<0.001); however, there was no correlation with IL-6 (p>0.05) (FIG. 2B). However, there was a correlation between plasma IL-17 and plasma IL-6 and IL-23 (FIG. 2C).

Surprisingly, we found that patients with fungal keratitis had a significantly higher percentage of IL-17 producing neutrophils and IL-17 gene expression than cohorts, which may be a result of corneal inflammation and cytokine production in response to growing hyphae. As predicted, the patient and cohort groups had a higher percentage of IL-17 expressing neutrophils than the control group. The presence of IL-17 producing neutrophils in healthy individuals also supports the concept that these cells are recruited to infected corneas rather than being generated at that site.

Although there were no differences in total plasma levels of IL-6, IL-17 and IL-23 among the study groups, when the data were combined for all individuals and correlation analyses were performed, we found a significant correlation between percentage IL-17 positive neutrophils and systemic IL-17 and IL-23, and a significant correlation between levels of plasma IL-17 and plasma IL-6 and IL-23. These findings are consistent with, though are not evidence of, their role in IL-17 production. Further, although recombinant IL-6 and IL-23 are sufficient to induce IL-17 expression by neutrophils, higher concentrations are required than found in the plasma, suggesting that that additional cytokines are also involved.

Patients with autoimmune diseases such as ANCA-associated vasculitis and ankylosing spondylitis also have very high serum IL-23 (3000-6000 pg/ml) compared with undetectable levels in normal individuals, and patients with Graves disease of the orbit have elevated IL-23 (>800 pg/ml) compared with normal individuals.

Approximately 80% peripheral blood neutrophils in healthy individuals in the USA constitutively express IL-6 and IL-23 receptors, and IL-17 gene expression is induced following incubation with recombinant IL-6 and IL-23. These cytokines also stimulate expression of a functional IL-17 receptor on neutrophils, and autocrine IL-17/IL-17 receptor activation mediates increased production of reactive oxygen species and fungal killing. Therefore, IL-17 producing neutrophils generated by long-term exposure to airborne conidia may limit the ability of *Aspergillus* and *Fusarium* to cause active infection, although they may also contribute to tissue damage, such as cornea ulcers.

Example 2

In example 1, we identified a distinct population of IL-17A expressing neutrophils in the cornea after fungal infection that are recruited to this site prior to Th17 cells, thereby representing an early IL-17 producing cell population in response to fungal infection. We also found RORγt-dependent, IL-17A expression in human peripheral blood neutrophils and murine bone marrow neutrophils after IL-6 and IL-23 stimulation. In this example, we examined the role of STAT3 phosphorylation in IL-17-producing-murine and human neutrophils. Further, we examined STAT3 phosphorylation, RORγt translocation, and IL-17 production in both murine and human neutrophils stimulated in vitro with IL-6 and IL-23. For in vivo murine studies, mice were sensitized to *Aspergillus* by subcutaneous injection of killed, swollen conidia prior to corneal infection with live conidia. This approach not only induced STAT3 phosphorylation, which was blocked by JAK2 and STAT3 inhibitors, but also inhibited RORγt translocation to the nucleus and IL-17 gene expression. In contrast, blocking this pathway had no effect on IL-17RC expression. We also demonstrate that JAK2 and STAT3 inhibitors blocked enhanced ROS production and fungal killing both in vitro and in a murine model of fungal keratitis.

Taken together, results of this example identify targets for therapeutic intervention in the multiple diseases in which these cells have been identified.

Experimental Procedures

*Aspergillus* strains—For cornea infections and in vitro fungal killing assays, an RFP expressing strain of *A. fumigatus* (Af-dsRed) was used. This strain is gpdA promoter driven to constitutively express monomeric dsRed. For subcutaneous "priming" injections, heat-killed, swollen conidia *Aspergillus fumigatus* strain Af-BP was used. For the *Aspergillus* hyphal extract used in ROS assay, *A. fumigatus* strain Af-BP hyphae were pulverized in liquid nitrogen, filtered through a 30 μm pre-separation filter (Miltenyi Biotec) and protein measured by the BCA method (Pierce). *Aspergillus* hyphal extracts (AspHE) were stored at −20° C. and used at a final concentration of 1 mg/ml.

Isolation of Murine Bone Marrow Neutrophils

Total bone marrow-derived cells were isolated from mouse femurs and tibias by flushing with RPMI and an 18-gauge needle. Erythrocytes were lysed with 1× lysis buffer (eBioscience), and bone marrow cells were separated on a Percoll (Fisher) gradient by density centrifugation (52%, 69%, and 78%). Cells at the 69-78% interface were harvested, and neutrophil purity (>98%) confirmed by flow cytometry and Wright-Giemsa staining.

Isolation of Peripheral Blood Human Neutrophils

Neutrophils were isolated from peripheral blood of healthy donors. Peripheral blood was incubated in 3% Dextran, and neutrophils isolated by Ficoll gradient centrifugation (Fisher Scientific), with neutrophil purity determined by staining with Wright-Giemsa.

Subcutaneous Injection (Priming) with Swollen, Heat-Killed Conidia

Live, plategrown *A. fumigatus* conidia were harvested and incubated for 6 h in Sabouraud dextrose broth to allow germination to occur and for expression of β-glucan, which initiates the host response. Heat-killed, swollen (germinated) conidia ($3\times10^8/100$ μl) were injected subcutaneously at the base of the tail. After 3 days, IL-17-producing neutrophils were confirmed by flow cytometry.

ELISA

IL-17A protein production was quantified by 2-site ELISA, according to the manufacturer's directions (R&D Biosciences).

In Vitro Activation of Murine and Human Neutrophils

Murine or human neutrophils were suspended at a density of 106 cells/ml and incubated with 20 μg/ml of recombinant mouse or human IL-6 and 2 μg/ml IL-23 in RPMI, and the cells were maintained for 1-3 h at 37° C. in 5% $CO_2$. Various inhibitors were used for assessing STAT3 activation. For STAT3, neutrophils were treated with either the STAT3-SH2 inhibitor, Stattic (20 μM) obtained from Tocris, or the JAK-1, 2 inhibitor, INC424, (aka Ruxolitinib; 20 μM (Selleck BioChem)). For the determination of RORγt-dependent signaling, SR1001 (20 μM; Sigma) was used, which inhibits RORγt binding to the IL-17 promoter site. All inhibitors were added to neutrophils 2 h prior to recombinant IL-6 and IL-23 stimulation.

Flow Cytometry

Corneas were dissected and incubated for 1 h at 37° C. in collaganese (80 U/ml) (C0130; Sigma-Aldrich), and washed in FACS buffer (PBS+1% FBS+0.5% Sodium azide). Ten corneas were pooled and analyzed by intracellular flow cytometry. Conversely, bone marrow cells or neutrophils were collected as described above and washed in FACS buffer. Corneal cells, total bone marrow cells, or isolated neutrophils were incubated (15 min) with anti-mouse CD16/32 antibody (Fc block, clone 93; eBioscience) or human Fc receptor binding inhibitor (eBioscience), washed and incubated (20 min) on ice with anti-mouse NIMP-R14 antibody (in-house) for cell surface markers. For intracellular staining, cells were incubated (20 min) in IC Fixation buffer (eBioscience), followed by permeabilizing buffer (eBioscience) for 1 h with anti-mouse/human-pSTAT3 Tyr705 (Cell Signal), STAT3, IL-17A, or RORγt antibodies (eBioscience) in the presence of Fc block. Cells were analyzed using a C6 Accuri flow cytometer (BD). Gating for flow cytometry was set based on isotype controls, except FIGS. 3F-H, which was gated on NIMP-R14+ neutrophils in the cornea. This allowed further studies of STAT3 and IL-17A to be performed on corneal neutrophils only (FIGS. 3F-H).

Confocal Imaging

Confocal images were collected using the UltraVIEW VoX spinning disk confocal system (Perkin Elmer, Waltham, Mass.) mounted on a Leica DMI6000B microscope equipped with HCX PL APO 100X/1.4 oil immersion objective using a 0.2 μm step size. Confocal images were then imported into Metamorph Image Analysis Software (Molecular Devices Corp., Downington, Pa.). Maximum projections were generated from the original stacks, which were subjected to 'no neighbors' 2D deconvolution.

Quantitative PCR

Neutrophil and corneal cell RNA was extracted using the RNeasy mini kit according to the manufacturer's directions (Qiagen, Valencia, Calif.). The quality of RNA was checked by spectrophotometry, and only samples with a 260/280 ratio of 2.0 were used to generate cDNA. The SuperScript First Strand synthesis system (Invitrogen) was used to generate cDNA according to the manufacturer's directions.

The SYBR green system (Applied Biosystems, Carlsbad, Calif.) was utilized for quantitative PCR (qPCR) using ABI Biosystems. PCR products were then run on a 1% agarose gel, and visualized using ethidium bromide. PCR products were compared to Actb (encoding the β-actin gene) or GAPDH as the controls for gel loading.

Western Blot of Cell Lysates and Nuclear Extracts

Neutrophils collected from primed or naïve C57BL/6 mice or unstimulated murine or human neutrophils were incubated with recombinant IL-6 and IL-23 for 60 min. After this time, cells were washed in PBS and lysed in ice-cold 1× lysis buffer (Cell Signaling Technology, Beverly, Mass.). Total protein was quantified using the BCA method, denatured with 2× Laemmli buffer (Sigma) and heated to 95° C. for 5 minutes. Nuclear extracts of the cells were prepared with the Pierce nuclear extract kit per the manufacturer's directions (Pierce). Ten μg of total protein was analyzed on a 12% SDS polyacrylamide gel, and transferred to nitrocellulose. Blots were probed with the following primary antibodies: Total STAT3 (R&D), p-STAT3 (R&D), RORγt (eBioscience), TATA box binding protein (TBP (Abcam)), and β-actin (Cell Signaling Technology). HRP-conjugated secondary antibodies were used (Santa Cruz Biotechnologies), and western blots developed with Supersignal West Femto Maximum Sensitivity Substrate (Pierce).

In Vitro Fungal Killing Assay

A hyphal coincubation assay was used to study the ability of murine and human neutrophils to inhibit *A. fumigatus* hyphal growth as described. Briefly, 12,500 *A. fumigatus* dsRed expressing conidia (strain Af-dsRed) per 200 μl Sabouraud dextrose media were added to wells of black-walled 96 well plates with an optically clear bottom (CoStar 3720). After 6 h, the conidia had germinated and the hyphae became adherent to the wells, at which time the medium was removed.

Murine and human neutrophils were incubated with p-STAT3 (20 μM Stattic or 20 μM INC424) or RORγt inhibitors (20 μM SR1001) for 2 h. Then the cells were stimulated with 20 μg/ml of rIL-6 and 2 μg/ml of rIL-23 for 3 h, washed, and 2×10$^5$ bone marrow-derived murine neutrophils or 10$^5$ human peripheral blood neutrophils, with or without recombinant IL-17A, were added to each well with growing hyphae. RPMI media was used as positive control (unimpaired growth), and PBS was used as a negative control (no growth (data not shown)). After 16 h the wells were washed with PBS and the dsRed fungal mass was quantified in a 96-well fluorometer at 550/600 nm excitation/emission filter (Synergy HT, Biotek).

Murine Models of Fungal Keratitis

C57BL/6 mice were primed and 3 days later cornea stroma was infected with 105 live conidia. Twenty-four hours post-infection, mice were euthanized and fungal growth in the cornea was imaged by fluorescence stereoscopy and quantified using Metamorph software. Infected corneas were also collected and digested with collaganese. The liberated corneal cells were incubated with NIMPR14 to quantify the number of neutrophils in the cornea. A sample size of 5 mice per group was analyzed.

In Vivo Blockade of STAT3 Phosphorylation

As previously described, phosphorylation of STAT3 was systemically inhibited. Briefly, 100 microliters of 0.8 mg INC424 (suspended in 20% DMSO and 80% polyethylene glycol 300) was administered by oral gavage twice per day over a 5-day period. C57BL/6 mice were primed 4 h after the last oral dose of INC424, and cornea stroma were infected 3 days after priming with 10$^5$ live RFP-expres sing *A. fumigatus* conidia. Systemic inhibition of STAT3 phosphorylation was confirmed in the bone marrow cells by flow cytometry.

Detection of ROS Production by CFDA

In vitro ROS production measured by CFDA was previously described. Briefly, 100 μg/100 μl of *A. fumigatus* hyphal extract (AspHE) were incubated with 2×10$^5$ murine or human neutrophils. Neutrophils were treated for 1 h with 1 μM Carboxyfluorescein diacetate (H2CFDA (Sigma)), which will fluoresce following ROS oxidation. Neutrophils were collected and analyzed by flow cytometry. H2CFDA pulsed neutrophils that had not been incubated with AspHE were used to set the ROS histogram gate. The average mean intensity was calculated by Accuri flow software and graphed in Prism.

Statistical Analysis

Statistical analysis was performed for each experiment using an unpaired t-test and one-way ANOVA analysis with Tukey's post-hoc analysis (Prism, GraphPad Software). A p-value<0.05 was considered significant.

Results

Phosphorylation of STAT3 in Neutrophils In Vivo

Figure 3A:
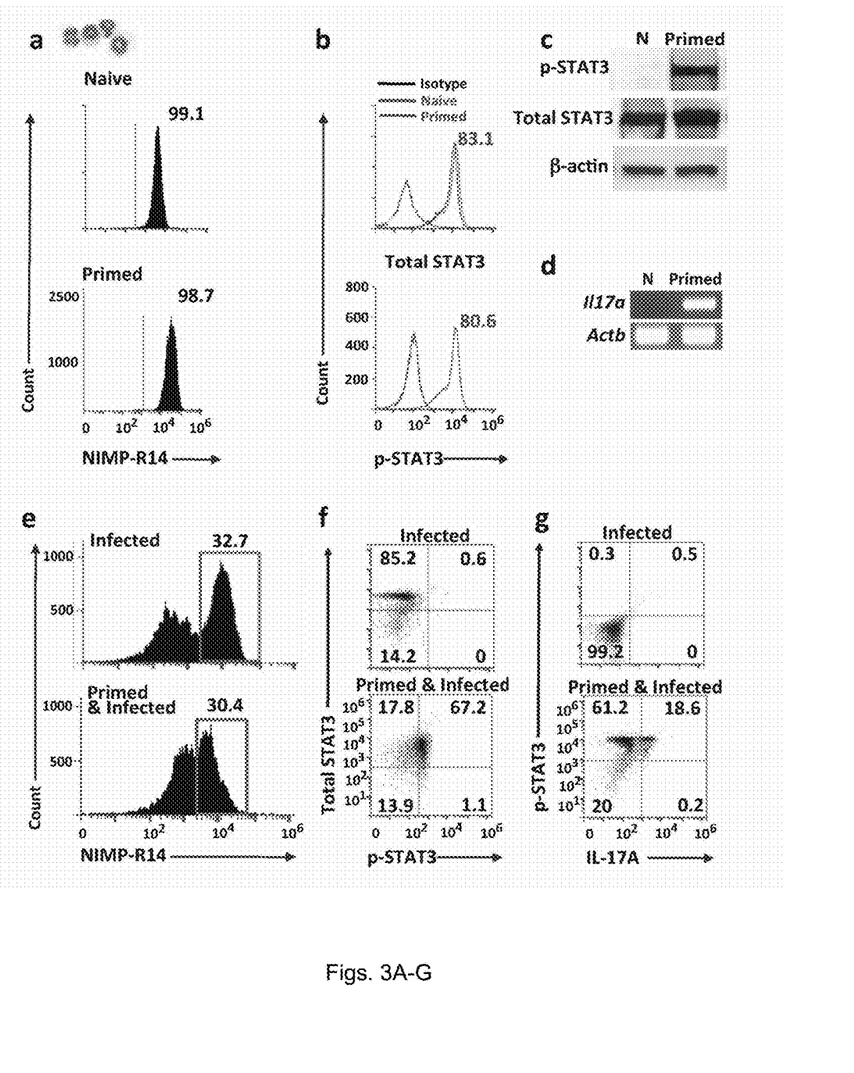

We demonstrated that a single immunization with heat-killed, swollen conidia induced systemic IL-6 and IL-23, and IL-17 producing neutrophils in the bone marrow within 72 h, prior to development of Th17 cells. To determine if STAT3 phosphorylation occurs in these neutrophils, C57BL/6 mice received a single subcutaneous injection of swollen, heatkilled *A. fumigatus* conidia. After three days, neutrophils were isolated from the bone marrow of C57BL/6 mice by gradient centrifugation, which yielded >98% neutrophils, as indicated by reactivity with the Ly6G antibody NIMP-R14 (FIG. 3A). These cells also had a characteristic polymorphonuclear morphology per Wright-Giemsa staining (FIG. 3A).

Total and phospho-STAT3 were detected by intracellular flow cytometry, and showed ~83.1% neutrophils of naïve and primed C57BL/6 mice expressing total STAT3 (FIG. 3B). In contrast, only neutrophils from primed mice expressed phospho-STAT3 (FIG. 3B). To confirm this finding, expression of total and phospho-STAT3 was also examined in cell lysates by Western blot analysis. As shown in FIG. 3C, neutrophils from naïve and primed mice, whereas p-STAT3 was only detected in neutrophils from primed mice. Consistent with these data and with our previous studies, IL-17a gene expression by quantitative PCR (qPCR) was detected in neutrophils from primed mice only (FIG. 3D).

To determine if p-STAT3 is expressed during infection, corneas were injected with live conidia, and after 24 h, neutrophils in infected corneas were examined by flow cytometry. (Primed mice more efficiently clear the infection.

There was no significant difference in the number of neutrophils recovered from primed compared with unprimed, infected corneas (FIG. 3E), and no significant difference between the groups in percent total STAT3 positive neutrophils. In contrast, only neutrophils from the primed, infected mice expressed p-STAT3 (67.2%, FIG. 3F), and all of the p-STAT3+ neutrophils were also IL-17 producing (FIG. 3G).

Taken together, these results demonstrate that p-STAT3 expression in murine neutrophils is only detected following priming, which we previously showed also induces IL-6 and IL-23 production.

Figure 4A:
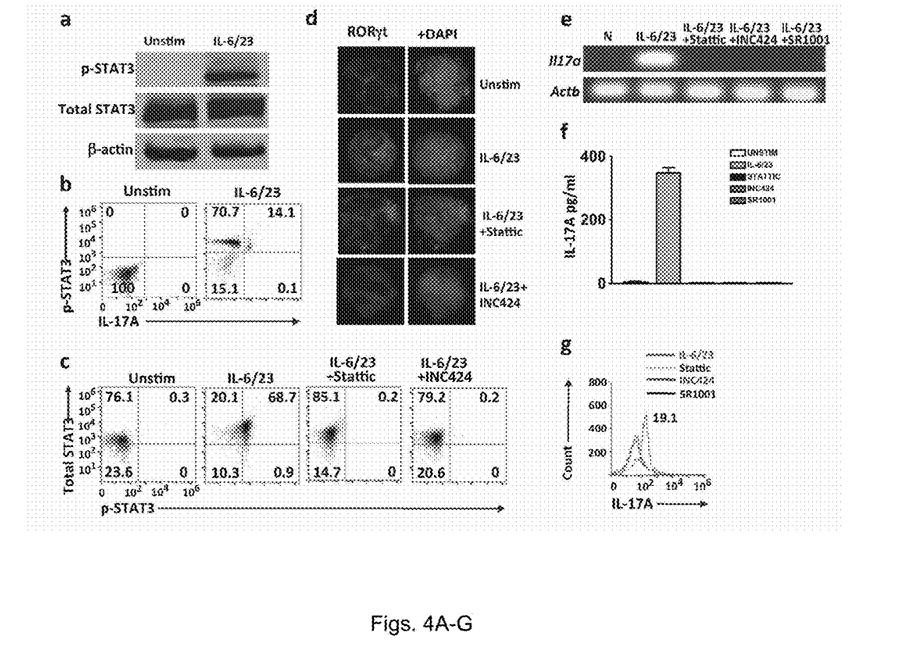

STAT3 Phosphorylation Mediates RORγt Nuclear Translocation and IL-17 Expression in Murine Neutrophils We demonstrated that recombinant (r)IL-6+IL-23 was sufficient to induce IL-17 expression in bone marrow neutrophils To examine the role of p-STAT3 in IL-17 producing neutrophils, bone marrow neutrophils from naïve C57BL/6 mice were incubated with 20 µg of IL-6 and 2 µg of IL-23 for 1 h, and STAT3 phosphorylation (p-STAT3) was examined in total cell lysates by immunoblot analysis. Although total STAT3 was detected in unstimulated (unstim) and IL-6/23 stimulated neutrophils. p-STAT3 was detected only in IL-6+IL-23-stimulated neutrophils (FIG. 4A). To ascertain if there is co-expression of p-STAT3 and IL-17A in IL-6+IL-23-stimulated neutrophils, intracellular, p-STAT3 and IL-17 were detected by intracellular flow cytometry. As shown in FIG. 4B, p-STAT3 and IL-17 were not detected in unstimulated neutrophils, whereas the p-STAT3 was found in >80% total neutrophils stimulated with IL-6+IL-23, and 14% of those cells also expressed intracellular IL-17A.

The RORγt transcription factor is constitutively expressed in a subpopulation of neutrophils, and translocates to the nucleus and is required for IL-17 expression in IL-6+IL-23-stimulated neutrophils. To examine the role of p-STAT3 in this process, bone marrow neutrophils from naïve C57BL/6 mice were incubated for 1 h with IL-6+IL-23 in the presence of p-STAT3 inhibitors, Stattic (which binds to the SH2 domain and inhibits phosphorylation or INC424, (Ruxolitinib, which selectively inhibits JAK-1 and JAK2 phosphorylation and hence p-STAT3, and RORγt nuclear translocation and IL-17 expression were evaluated. Stattic and INC424 completely inhibited p-STAT3 in IL-6/23 stimulated neutrophils (FIG. 4C). RORγt was detected in the cytoplasm in unstimulated neutrophils, but was present in the nucleus following IL-6+IL-23 stimulation; however, RORγt was only detected in the cytoplasm when stimulated cells were incubated with Stattic or INC424 (FIG. 4D).

IL-17 is not expressed in IL-6+IL-23 stimulated neutrophils from RORγt homozygous knock-in mice (RORcgfp/gfp) mice, which do not express RORγt. To determine the effect of RORγt inhibitors on IL-17 expression, neutrophils were incubated with IL-6+IL-23 and with SR1001, which blocks RORγt binding to the Il17a promoter. As shown in FIGS. 4E-G, Il17a gene expression, total IL-17A protein, and intracellular IL-17A were detected in IL-6+IL-23 stimulated neutrophils, but not in the presence of the SR1001 RORγt inhibitor or p-STAT3 inhibitors.

Together, these findings demonstrate that phosphorylation of STAT3 induces RORγt translocation to the nucleus, which is required for IL-17A production in murine neutrophils.

Figure 5A:
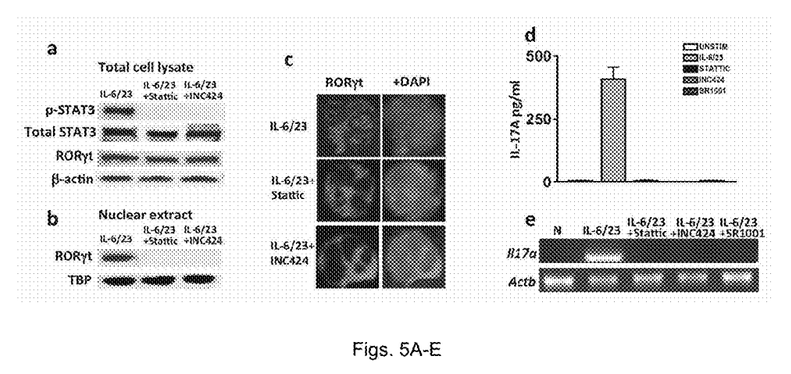

Phosphorylation of STAT3 Mediates RORγt Translocation and IL-17 Production in Human Neutrophils We examined if phosphorylation of STAT3 induced translocation of RORγt and IL-17 production in human neutrophils. A highly purified population of peripheral blood neutrophils were isolated by gradient centrifugation, and incubated with recombinant human IL-6 and IL-23 (IL-6/23) for 1 h. Total neutrophil lysate and nuclear extract were isolated for western blot analysis of STAT3, p-STAT3 and RORγt. As shown in FIG. 5A, p-STAT3 was inhibited by Stattic and INC424, whereas total STAT3 and RORγt expression were not altered. However, when phosphorylation of STAT3 was inhibited by either Stattic or INC424, RORγt was no longer detectable from nuclear extracts from IL-6/23-stimulated neutrophils (FIG. 5B).

To further examine the role of p-STAT3 on the translocation of RORγt, from cytosol to nucleus, purified human neutrophils were incubated with recombinant human IL-6 and IL-23 in the presence of Stattic and INC424, then stained with anti-RORγt antibody and the cells examined by confocal microscopy. RORγt was detected in the nucleus of IL-6/23-stimulated neutrophils, but RORγt was only detected in the cytoplasm in IL-6/23-neutrophils in the presence of p-STAT3 inhibitors (FIG. 5B). In addition, inhibition of p-STAT3 by either Stattic or INC424 in IL-6/23-stimulated neutrophils ablated IL-17A protein (FIG. 5D) and Il17a gene expression (FIG. 5E). Together these findings demonstrate that, similar to murine neutrophils, the phosphorylation of STAT3 is IL-6 and IL-23-dependent. Moreover, in human neutrophils the phosphorylation of STAT3 is a mechanism required to translocate RORγt from the cytoplasm to the nucleus, which is also required the synthesis of IL-17.

Figure 6A:
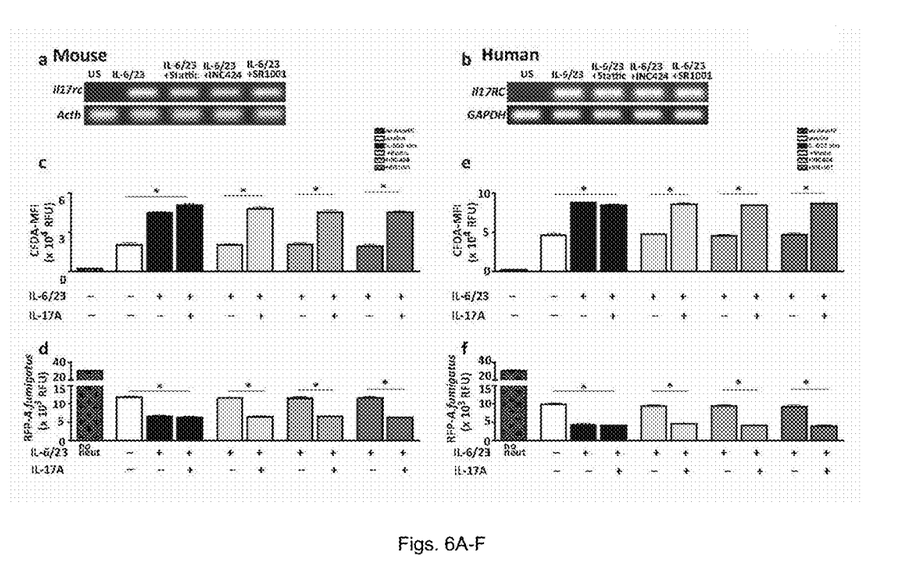

Phosphorylation of STAT3 and IL-17 Production Mediates Enhanced ROS Production and Fungal Killing The dimer form of the IL-17 receptor is comprised of two subunits: IL-17RA and IL-17RC. Previous studies have shown that both human and mouse neutrophils constitutively express the IL-17RA portion of the IL-17 receptor and IL-17 downstream signaling pathway Act1. We discovered that IL-6/23-stimulated neutrophils induced the expression of the IL-17RC subunit and furthermore that IL-17 signaling was fully functional in these stimulated neutrophils. However, the mechanism by which IL-6/23-stimulation causes induction of IL-17RC expression had not yet been determined. Therefore, to determine if STAT3 has a role in IL-17 receptor expression in IL-6/23-stimulated neutrophils, neutrophils were stimulated for 1 h with recombinant IL-6 and IL-23 in the presence of Stattic, INC424 or SR1001, and IL-17RC gene expression was analyzed by qPCR. The results (FIGS. 6A, B) showed that inhibition of p-STAT3 or RORγt signaling did not inhibit IL-17RC expression in IL-6/23-stimulated murine or human neutrophils.

When neutrophil IL-17RC is expressed, IL-17A signaling can cause increased production of reactive oxygen species (ROS), whereas ROS production by neutrophils limits the growth of filamentous hyphae (such as Aspergillus). In that regard, we next examined the role of STAT3, RORγt, and IL-17 in ROS production and in fungal killing using an in vitro assay. Neutrophils were stimulated with recombinant mouse IL-6 and IL-23 with or without p-STAT3 or RORγt inhibitors 3 h prior to incubating the cells with A. fumigatus hyphae. ROS production was measured at the intracellular level of amine-reactive fluorescent diacetate CFDA, and dsRed-expressing fungal mass was quantified by fluorimetry as previously described. As previously reported ROS was produced 1 h after hyphal stimulation and was elevated in IL-6/23-stimulated bone marrow-derived murine neutrophils, with no increase in ROS after the addition of rIL-17A (FIG. 6C). In contrast, ROS production was not increased above the level produced by naïve neutrophils in p-STAT3 or RORγt inhibited neutrophils (i.e., +Stattic, +INC424, +SR1001) after IL-6/23-stimulation (FIG. 6C). However, ROS production was increased in these stimulated-inhibited murine neutrophils after further stimulation with rIL-17A (FIG. 6C). Conversely, the fluorescent fungal mass of RFP-expressing A. fumigatus was reduced after incubation with naïve neutrophils, which was further, decreased when naïve neutrophils were stimulated recombinant mouse IL-6 and IL-23 (FIG. 6C). Phospho-STAT3 and RORγt-inhibited neutrophils did not further impede hyphal growth when stimulated with recombinant mouse IL-6 and IL-23. However, when these neutrophils were incubated with rIL-17A enhanced hyphal killing activity was detected (FIG. 6D). Human peripheral blood neutrophils stimulated with recombinant human IL-6 and IL-23 in the presence of p-STAT3 (Stattic or INC424) or RORγt (SR1001) inhibitors had the same phenotype as murine neutrophils in that IL-6/23 stimulation increased ROS production (FIG. 6E) and fungal mass was decreased more than unstimulated neutrophils (FIG. 6F). However, when p-STAT3 or RORγt signaling was inhibited no increase in ROS (FIG. 6E) or decrease in fluorescent fungal mass was detected beyond what was detected in unstimulated neutrophils (FIG. 6F). This latter finding was reversed when neutrophils were incubated with rhIL-17A, whereas increased ROS and decreased fungal mass was detected in the p-STAT3 and RORγt-inhibited human neutrophils in the presence of IL-17A (FIG. 6E, F). Overall, these results indicated that phosphorylation of STAT3 and RORγt signaling were both required for IL-17 to enhance ROS production and fungal killing.

Inhibition of Fungal Growth is Dependent on Phosphorylation of STAT3 In Vivo

Figure 7A:
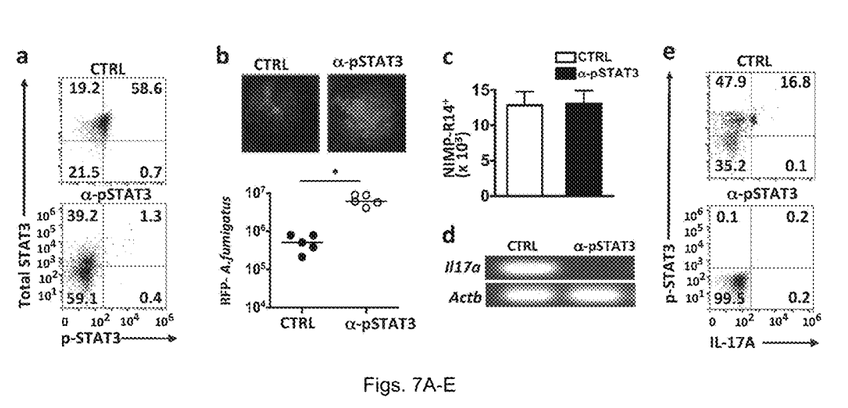

To determine if phosphorylation of STAT3 is required for IL-17-producing neutrophils to regulate fungal growth in vivo, STAT3 phosphorylation was blocked in C57BL/6 mice by administering INC424 to mice (0.8 mg/ml) by oral gavage twice a day for 5 consecutive days prior to priming the mice with heat-killed, swollen conidia to generate IL-17-producing neutrophils. After 72 h, live RFP-expressing *A. fumigatus* conidia were injected into the cornea stroma of primed C57BL/6 mice, and RFP-expressing hyphae was quantified 24 h post-infection in the cornea by image analysis. The systemic blockade of p-STAT3 was confirmed by flow cytometry analysis of total STAT3/p-STAT3 in total bone marrow cells (FIG. 7A). Primed, infected C57BL/6 mice (CTRL) had significantly lower RFP-fungal mass than p-STAT3 inhibited-primed-infected C57BL/6 mice (α-pSTAT3) (FIG. 7B). Although there was no difference in the total number of neutrophils infiltrating the infected corneas (FIG. 7C), gene expression of Il17a was detected only in the corneal cells of the primed, infected (CTRL) mice and not in the pSTAT3 inhibited-primedinfected (α-pSTAT3) mice (FIG. 7D). Further, p-STAT3/IL-17-producing neutrophils were only identified in the corneas of primed-infected mice (CTRL) and neutrophils were the sole source of IL-17 in those infected corneas (FIG. 7E). These data indicate that enhanced fungal killing in vivo by IL-17-producing neutrophils was dependent on the phosphorylation of STAT3.

We show a role for p-STAT3 in the nuclear translocation of RORγt and the production of IL-17 by murine and human neutrophils. A subpopulation of RORγt expressing neutrophils was discovered which could be induced to produce IL-17 after stimulation with IL-6/23 in vitro or after priming mice with *Aspergillus* heat-killed spores in vivo. Furthermore, these IL-17 producing, RORγt-expressing neutrophils have also been identified in the skin lesions of psoriasis patients. STAT3 and RORγt have well characterized roles in generating IL-17 production by Th17 cells, but the role of p-STAT3 in IL-17-producing neutrophils had not yet been fully defined until now.

In lymphoid cells, both IL-23 and IL-6 can activate the phosphorylation of STAT3, which was shown to mediate IL-17 production In the presence of G-CSF, neutrophils can signal through the Jak 1 and Jak 2 tyrosine kinases to phosphorylate STAT3. This event enhances production of chemokines and chemokine receptor expression in bone marrow-derived neutrophils. Using the Jak1/Jak2 inhibitor, INC424, or STAT3-SH2 inhibitor, Stattic, we demonstrated that IL-17 production in neutrophils was STAT3 dependent.

STAT3 also plays a role in initiating Th17 cell differentiation by inducing RORγt expression. Unlike Th17 cells, a subset of neutrophils constitutively expresses RORγt, which is also true of innate lymphoid cells like γδcells. Although the phosphorylation of STAT3 does not induce neutrophil RORγt expression, p-STAT3 does interact directly with RORγt to induce IL-17 production in neutrophils. By inhibiting STAT3 phosphorylation, we found that RORγt translocation to the nucleus was p-STAT3 dependent. In lieu of RORγt translocation, IL-17 is not produced in IL-6/23-stimulated neutrophils. Moreover, in IL-23-stimulated Th17 cells, p-STAT3 can directly induce IL-17 production in a RORγt-independent fashion. In contrast, IL-17 production in stimulated neutrophils was ablated in the presence of SR1001 inhibitor (a synthetic ligand that inhibits the binding of RORγt to the IL-17 promoter site). This result showed that unlike Th17 cells, IL-17 production by IL-6/23 stimulated neutrophils was completely RORγt-dependent.

In addition to IL-17 production, IL-6/23 stimulation also induces expression of the IL-17RC subunit of the IL-17 receptor. As neutrophils constitutively express IL-17RA, IL-6 and IL-23 stimulation therefore induce expression of a functional IL-17 receptor on these cells. However, IL-17RC expression is not RORγt or p-STAT3-dependent so that future studies will be needed to identify the signaling pathways involved in the expression of the IL-17RC receptor.

Although p-STAT3 did not apparently play a role in IL-17 receptor expression, p-STAT3 did regulate the production of IL-17 and the autocrine signaling that induces increased ROS production and enhanced fungal killing. When STAT3 phosphorylation was inhibited, an increase in the production of ROS was not seen nor was the enhanced fungal killing normally observed in stimulated neutrophils. Thus, antimicrobial activity was controlled by IL-17 signaling, which was confirmed when recombinant IL-17 was added to the p-STAT3 or RORγt-inhibited neutrophils in vitro. Importantly, enhanced fungal killing and increased ROS was observed in the presence of recombinant IL-17.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, I claim:

1. A method of treating a corneal ulcer from fungal infection in a subject comprising
   administering to peripheral blood of the subject a therapeutically effective amount of an agent that inhibits STAT3 mediated IL-17 expression in neutrophils of the subject, wherein the agent comprises the STAT3 inhibitor INC424 and a RORγt inhibitor SR1001.

2. The method of claim 1, the fungal infection selected from an *Alternaria, Aspergillus, Candida, Curvularia, Fusarium*, or *Histoplasma* fungal infection.

3. The method of claim 1, the agent being administered to the subject in conjunction with one or more additional therapeutic agents.

4. The method of claim 3, the one or more additional therapeutic agents comprising an antibiotic, antiviral or antifungal agent.

\* \* \* \* \*

UNITED STATES PATENT AND TRADEMARK OFFICE
CERTIFICATE OF CORRECTION

| | | |
|---|---|---|
| PATENT NO. | : 9,814,720 B2 | |
| APPLICATION NO. | : 14/837893 | |
| DATED | : November 14, 2017 | |
| INVENTOR(S) | : Eric Pearlman | |

It is certified that error appears in the above-identified patent and that said Letters Patent is hereby corrected as shown below:

In the Specification

Column 1, Line 12 Please add the following paragraph:
--GOVERNMENT FUNDING
This invention was made with government support under EY018612 awarded by The National Institutes of Health. The government has certain rights in the invention.--

Signed and Sealed this
Twenty-fifth Day of June, 2024

Katherine Kelly Vidal
*Director of the United States Patent and Trademark Office*